Figure 1:
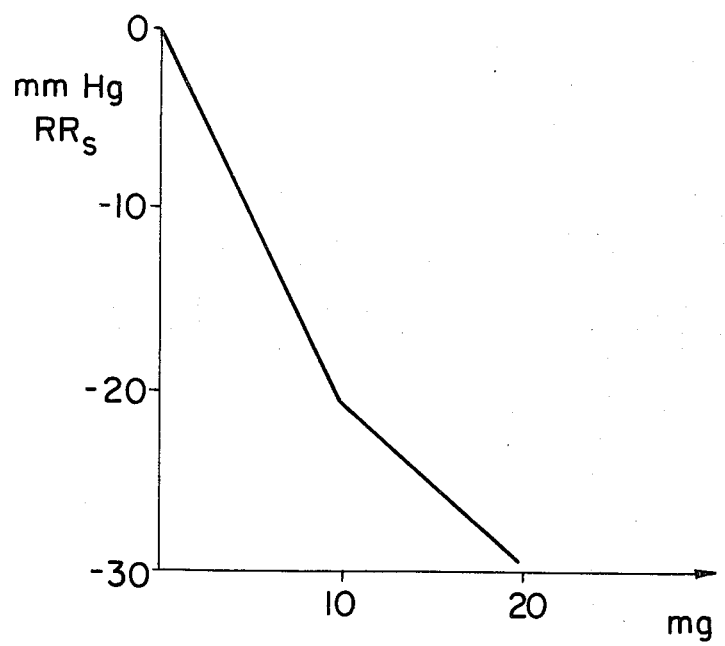

United States Patent [19]
Amschler et al.

[11] 3,984,555
[45] Oct. 5, 1976

[54] THERAPEUTIC PIPERAZINYLALKYL-QUINAZOLONE-(4)-DERIVATIVES

[75] Inventors: Hermann Amschler, Constance; Wolfgang Schoetensack, Hegne; Kurt Klemm, Allensbach, all of Germany

[73] Assignee: Byk Gulden Lomberg Chemische Fabrik Gesellschaft mit beschrankter Haftung, Constance, Germany

[22] Filed: May 28, 1971

[21] Appl. No.: 148,100

[30] Foreign Application Priority Data
June 5, 1970   Germany............................ 2027645

[52] U.S. Cl............................. 424/251; 260/251 Q
[51] Int. Cl.²......................................... A61K 31/505
[58] Field of Search...,........................... 424/258, 251

[56] References Cited
FOREIGN PATENTS OR APPLICATIONS
1,231,705   1/1967   Germany..................... 260/256.4 Q OTHER PUBLICATIONS
Chem. Abst., (1), 68–29720z (1968).
Chem. Abst., (2), 68–103738e (1968).

*Primary Examiner*—Sam Rosen
*Attorney, Agent, or Firm*—Toren, McGeady and Stanger

[57] ABSTRACT

Aryl-substituted piperazinylalkyl-quniazolone-(4) derivatives suitable for use as hypotensive, antihistaminic, and analgesic drugs are described. Process for the preparation of the compounds by (1) intra molecular condensation of the product obtained from the reaction of a halogen carboxylanilide with an aryl piperazine; (2) reaction of an ω-halogen-alkyl quinazolone with an aryl piperazine; or (3), reaction of an anthranilic acid with a (4-aryl-piperazinyl-(1) carboxylamide, nitride, amidine, or iminoester, followed by alkylation of the product.are also described. Pharmaceutical compositions containing the compounds and halogenalkanoic acid-6-carbamyl anilides useful for preparing the compounds are disclosed.

6 Claims, 2 Drawing Figures

THERAPEUTIC PIPERAZINYLALKYL-QUINAZOLONE-(4)-DERIVATIVES

The invention relates to therapeutically valuable arylsubstituted piperazinylalkyl quinazolone-(4) derivatives with predominantly hypotensive properties.

For a fairly long time quinazolone-(4) derivatives have been known with sedative (Therapie, Vol. 13, (1958), pp. 30 to 45) and anticonvulsive properties (Journal of Pharmacy and Pharmacology, Vol. 12 (1960), p. 501). Of the quinazolone-(4) derivatives described in German Published patent application No. 1,231,705 and 1,249,281 2-dimethylaminomethyl-3-methyl-6-ethoxyquinazolone-4 possesses an analgesic action which is comparable with that of the known 4-dimethylamino-1-phenyl-2,3-dimethylpyrazolone-5.

The present invention relates to aryl-substituted piperazinylalkyl-quinazolone-(4) derivatives of the general formula I and their salts of pharmacologically tolerable inorganic or organic acids:

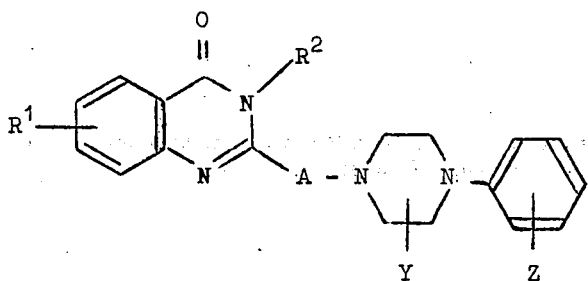

I

In the general formula I:

$R^1$ signifies a hydrogen atom, a halogen atom, such as a fluorine or iodine, especially a chlorine or bromine atom, one to three straight-chained or branched, saturated or unsaturated alkyl groups with 1 to 6 carbon atoms or one to three straight-chained or branched, saturated or unsaturated alkoxy groups with 1 to 6 carbon atoms;

$R^2$ signifies a hydrogen atom, a straight-chained or branched, saturated or unsaturated alkyl group, a phenyl alkyl group or a cycloalkyl group each with 1 to 6 carbon atoms;

A signifies a straight-chained or branched, saturated or unsaturated alkylene group with 1 to 6 carbon atoms;

Y signifies a hydrogen atom or an alkyl group with 1 to 4 carbon atoms and

Z signifies a hydrogen atom or one or more alkyl, alkoxy or alkylmercapto groups each with 1 to 4 carbon atoms, trifluoromethyl groups or fluorine, chlorine or bromine atoms.

Straight-chained or branched, saturated or unsaturated alkyl groups with 1 to 6 carbon atoms suitable as $R^1$ and $R^2$ are, for example, methyl, ethyl, propyl, isopropyl, butyl, isobutyl, sec.-butyl, tert.-butyl, pentyl, isopentyl, 1- or 2-methylbutyl, tert.-pentyl, hexyl, isohexyl, 1-, 2- or 3-methylpentyl, 1-, 2- or 3-ethylbutyl, 1,2-, 1,3- or 2,3-dimethyl-butyl group, a vinyl, allyl, 2-methyl-allyl, propen-1-yl, buten-1-yl, or buten-2-yl, penten-1-, 2- or 3-yl, hexenyl, 2-methyl-propyn-1-yl or propin-1- or 2-yl.

Straight-chained or branched, saturated or unsaturated alkoxy groups with 1 to 6 carbon atoms suitable as $R^1$ are for example, an alkoxy group derived from one of the abovementioned alkyl groups with 1 to 6 carbons atoms, such as for example, a methoxy, ethoxy, propoxy, isopropoxy, butoxy, isobutoxy, sec.-butoxy, tert.-butoxy, pentyloxy, isopentyloxy, 1- or 2-methylbutyloxy, tert.-pentyloxy, hexyloxy, isohexyloxy, allyloxy, 2-methyl-allyloxy or buten-2-yloxy group.

Phenyl alkyl groups suitable as $R^2$, in which the alkyl group contains 1 to 6 carbon atoms are, for example, benzyl or an $\alpha$- or $\beta$-phenylethyl group. Cycloalkyl groups with 1 to 6 carbon atoms suitable as $R^2$ are, for example, cyclopropyl, cyclopentyl, 2- or 3-methylcyclopentyl, cyclohexyl or cyclohexenyl.

Straight-chained or branched, saturated or unsaturated alkylene groups with 1 to 6 carbon atoms suitable as A are, for example, methylene, 1,1-ethylene, 1,2-ethylene, trimethylene, propylidene, 1- or 2-methylethylene, propen-1 or 2-ylene, tetramethylene, 1-, 2- or 3-methyltrimethylene, butylidene, 1- or 2-ethylethylene, buten-2-ylene, pentylidene, pentamethylene or hexamethylene group, and also a 1-, 2-, 3- or 4-methyltetramethylene, 1- or 2-propylethylene, 1- or 2-isopropyl-ethylene, 1-, 2- or 3-ethyl-trimethylene, 1-methyl-2-ethyl-ethylene, 2-methyl-1-ethyl-ethylene, 1,3- dimethyl-trimethylene, pentadien-1,3-ylene, hexylidene, 1- or 2-butyl-ethylene, 1- or 2-isobutyl-ethylene, 1- or 2-sec.-butyl-ethylene, 1- or 2-tert.-butyl-ethylene, 1-, 2- or 3-propyltrimethylene, 1-, 2- or 3-isopropyl-trimethylene, 1-, 2-, 3- or 4-ethyl-tetramethylene, 1-, 2-, 3- or 4-ethyl-tetramethylene, 1-, 2-, 3, 4- or 5-methyl-pentamethylene, 1,2-, 1,3-, 2,3-, 3,4- or 2,4-dimethyltetramethylene, 1-methyl-3-ethyl-trimethylene, 1,2,3-trimethyltrimethylene, 1-methyl-2-ethyl-trimethylene, 3-methyl-1-ethyl-trimethylene, 2-methyl-1-ethyl-trimethylene, 2-methyl-3-ethyl-trimethylene, hexatrien-1,3,5-ylene or hexen-2- or 3-ylene.

Alkyl groups with 1 to 4 carbon atoms suitable as the radicals Y and Z are methyl, ethyl, propyl, isopropyl, butyl, isobutyl, sec.-butyl or tert.-butyl.

Alkoxy or alkylmercapto groups with 1 to 4 carbon atoms suitable as Z are methoxy, ethoxy, propoxy, isopropoxy, butoxy, isobutoxy, sec.-butoxy or tert.-butoxy group or a corresponding mercapto compound, such as for example methylmercapto, ethylmercapto, propylmercapto, isopropylmercapto or butymercapto.

The compounds according to the invention having the general formula I constitute valuable pharmaceutical products which, unlike the known compounds of a similar structure, are characterised especially by hypotensive, antihistaminic and analgesic actions. The analgesic actions correspond to those of morphine and are 30 to 40 times as great as those of the compounds described in German Pat. Applications Nos. 1,231,705 and 1,249,281.

From this class of compounds, particularly good effects are possessed by aryl-substituted piperazinyl alkyl quinazolone-(4) derivatives of the general formula I* and their salts of pharmacologically compatible inorganic or organic acids,

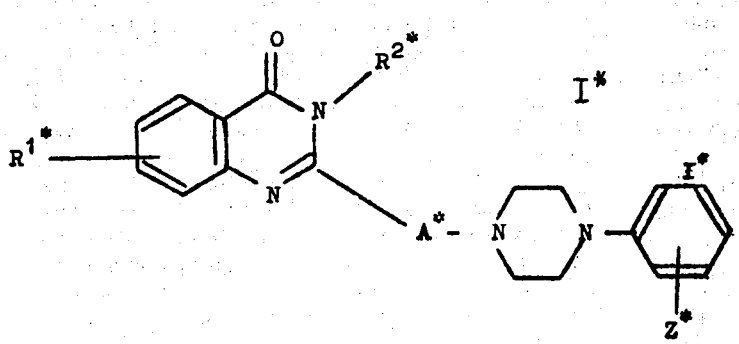

in which
R¹* signifies 1 to 2 methyl, ethyl, methoxy or ethoxy groups, especially in the 6 and/or 7 position;
R²* is a hydrogen atom or a methyl or ethyl group;
A* is an ethylene or trimethylene group; and
Z* is a fluorine or chlorine atom or a methyl or alkoxy group with 1 to 4 carbon atoms;
particularly preferable compounds include: 2-(2-(1-tolyl)-piperazinyl-4)ethyl)-6,7-dimethoxy-4(3H)-quinazolone, 2(2-(1-(3-tolyl)piperazinyl-4)ethyl)-6,7-dimethoxy-4-(3H)-quinazolone, 2-(2-(4-tolyl)piperazinyl-4)ethyl)-6,7-dimethoxy-4(3H)-quinazolone, 2-(2-(1-(3-methoxyphenyl)piperazinyl-4)ethyl)-6,7-dimethoxy-4(3H)-quinazolone, 2-(2-(1-(2-methoxyphenyl) piperazinyl-4)ethyl)-3-methyl-6,7-dimethoxy-4(3H)-quinazolone, 2-(2-(1-(2-ethoxyphenyl) piperazinyl-4)-ethyl)-6,7-dimethoxy-4(3H)-quinazolone, 2-(2-(1-(2-chlorophenyl) piperazinyl-4) ethyl)-6,7-dimethoxy-4(3H)-quinazolone, 2-(2-(1-(3-chlorophenyl) piperazinyl-4) ethyl)-6,7-dimethoxy-4(3H)-quinazolone, 2-(2-(1-(4-chlorophenyl) piperazinyl-4) ethyl)-6,7-dimethoxy-4(3H)-quinazolone, 2-(2-(1-(2-fluorophenyl) piperazinyl-4) ethyl)-6,7-dimethoxy-4(3H)-quinazolone, 2-(2-(1-(3-fluorophenyl) piperazinyl-4)ethyl)-6,7-dimethoxy-4(3H)-quinazolone, 2-(2-(1-(4-fluorophenyl) piperazinyl-4) ethyl)-6,7-dimethoxy-4(3H)-quinazolone, 2-(2-(1-(4-methoxyphenyl) piperazinyl-4) ethyl)-6,7-dimethoxy-4(3H)-quinazolone, 2-(1-(2-methoxyphenyl) piperazinyl-4)methyl-6,7-dimethoxy-4(3H)-quinazolone and 2-(3-(1-(2-methoxyphenyl)-piperazinyl-4)-n-propyl)-6,7-dimethoxy-4(3H)-quinazolone, especially 2-(2-(1-(2-methoxyphenyl)-piperazinyl-4)-ethyl)-6,7-dimethoxy-4(3H)-quinazolone, and also their salts of pharmacologically compatible inorganic or organic acids.

The invention also relates to a process for the production of the compounds of the general formula I, wherein
a. a halogen carboxylanilide of the general formula II, in which R¹, R² and A have the meanings given above and Hal signifies a halogen atom — preferably a chlorine or bromine atom — is reacted with an aryl piperazine of the general formula III,

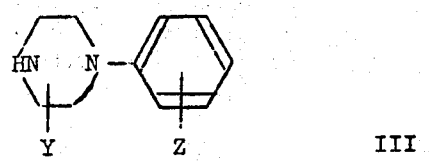

in which Y and Z have the meanings given above, and the compound of the general formula IV

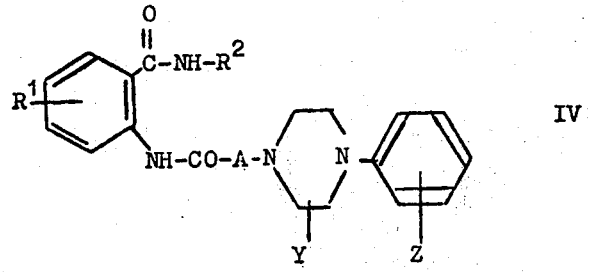

so obtained in which R¹, R², A, Y and Z have the meanings given above, is intramolecularly condensed at elevated temperature; or
b. an ω-haogen-alkyl quinazolone of the general formula V,

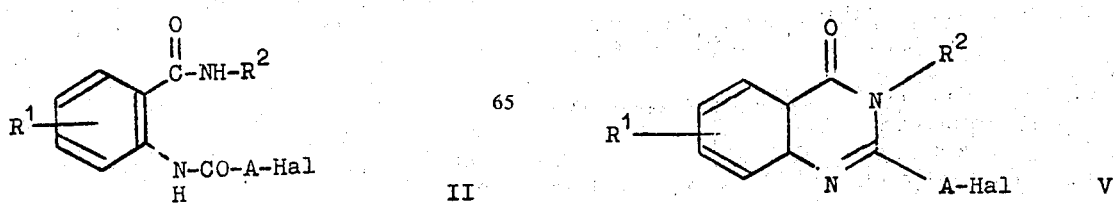

in which R¹, R², A and Hal have the meanings given above, is reacted with an aryl piperazine of the general formula III; or c. an anthranilic acid of the general formula VI

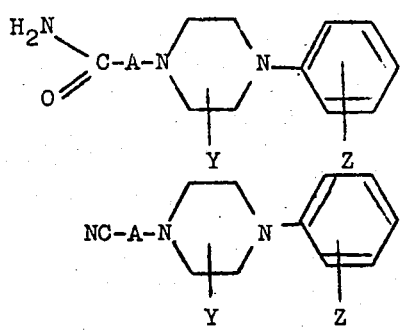

VI in which R¹ has the meaning given above, or a reactive ester of such a compound is reacted with a compound of the general formula VII, VIII or IX

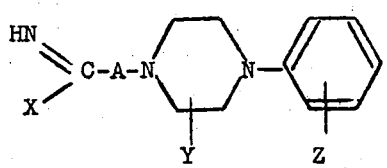

VII

VIII

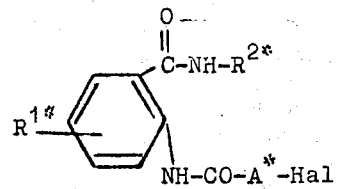

IX in which A, Y and Z have the meanings given above and X is an amino group or an alkoxy group with 1 to 4 carbon atoms, at elevated temperature, and, if desired, the radical R² is introduced into the compound so obtained by alkylation.

If desired, the compounds obtained according to (a), (b) and (c) may be converted into the salts of pharmacologically compatible inorganic or organic acids or alternatively, a salt if obtained may be converted into the free compound.

Preferably one reacts:

a. compounds of the general formula II*

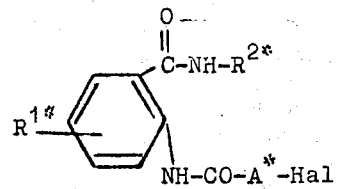

II* with aryl piperazines of the general formula III*

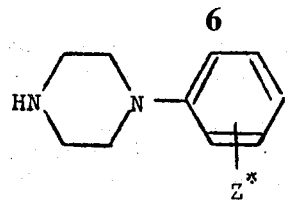

III* in which R¹⁼, R²⁼, A* and Z* and Hal have the meanings given above; or b. an ω-halogen alkyl quinazolone of the general formula V*

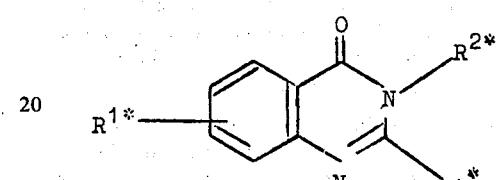

V* in which R¹*, R²* and A* have the meanings given above, with an aryl piperazine of the general formula III*; or c. an anthranilio acid of the general formula VI*

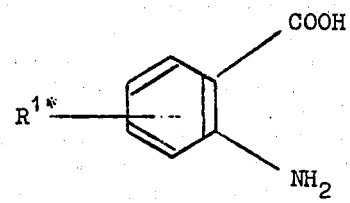

or a reactive ester of such a compound, with a compound of the general formula VII*, VIII* or IX*

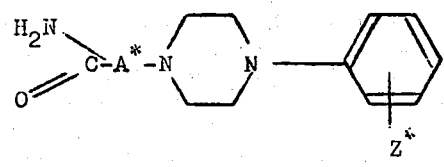

VII*

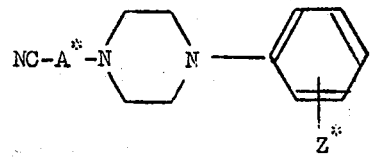

VIII*

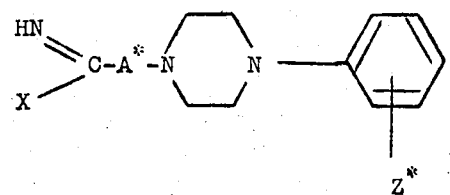

IX* and wherein, if desired one introduces the radical R²*, R¹*, R²*, A* and Z* and X having the meanings given above.

In the first stage of the process according to (a), the reaction of the compounds of the general formula II with aryl piperazines of the general formula III, may be carried out in the presence of an inert organic solvent, for example, alcohols, such as, ethyl alcohol, isopropyl alcohol, ketones, such as, acetone, methylethylketone, strongly polar fatty acid amides or nitriles, such as, dimethylformamide, dimethyl acetamide, acetonitrile or mixtures thereof, at temperatures between 50° and 120° C, and especially between 50° and 70° C. In such cases it is advantageous to use an equivalent quantity of an auxiliary base, such as, triethylamine, ethyldicyclohexylamine, dicyclohexylamine or potassium carbonate, or to carry out the reaction with at least double the equivalent quantity of aryl piperazine whether or not the solvents mentioned above are used.

As halogencarboxylanilides of the general formula II one can use, for example: the 2-carbamyl anilides of chloracetic, bromacetic or iodoacetic acid, of 2- or 3-(chloro- or bromo-) propionic acid, of 2-, 3- or 4-(chloro or bromo-) butyric acid, of 2-, 3-, 4- or 5-(chloro-or bromo-) valeric acid, of 2-, 3-, 4-, 5- or 6-(chloro- or bromo-) caproic acid, of 2-, 3-, 4-, 5-, 6- or 7-(chloro- or bromo-) oenanthic acid, of 2-methyl-3-(chloro- or bromo-) butyric acid, of 2-ethyl-4-(chloro- or bromo-) butyric acid, of 3-ethyl-4-(chloro- or bromo-) butyric acid, of 4-chloro- or 4-bromo-crotonic acid; the 4- or 5-methyl-2-carbamyl anilides, the 4- or 5-ethyl-2-carbamyl anilides, the 4- or 5-propyl-2-carbamyl anilides, the 4,5-dimethyl or 4,5,6-trimethyl-2-carbamyl anilides, the 4- or 5-(chloro- or bromo-)-2-carbamyl anilides, the 4- or 5-(methoxy, ethoxy-, propoxy-, isopropoxy-, butoxy-, isobutoxy-, sec.-butoxy-, tert.-butoxy- or allyloxy)-2-carbamyl anilides, the 4,5- or 5,6-(dimethoxy- or diethoxy-)-2-carbamyl-anilides, the 4,5,6-trimethoxy-2-carbamyl anilides or the 2-(N-methylcarbamyl, N-ethylcarbamyl, N-propylcarbamyl, N-isopropylcarbamyl, N-butylcarbamyl, N-pentylcarbamyl, N-isopentylcarbamyl, N-benzylcarbamyl, N-(β-phenylethyl)-carbamyl, N-cyclopropylcarbamyl, N-cyclopentylcarbamyl or N-cyclohexylcarbamyl)-4,5-dimethoxy anilides of the acids mentioned above.

Halogencarboxylanilides which are preferably used are those of the general formula II*, for example, the 2-(carbamyl, N-methylcarbamyl or N-ethylcarbamyl)-4- or 5-(methyl- or ethyl-) anilides, the 2-(carbamyl, N-methylcarbamyl or N-ethylcarbamyl-)-4- or 5-(methoxy- or ethoxy)-anilides; or the 2-(carbamyl, N-methylcarbamyl or N-ethylcarbamyl)-4,5-(dimethoxy- or diethoxy)-anilides of 3-(chloro- or bromo)-propionic acid or of 4-(chloro- or bromo)-butyric acid.

As aryl piperazines of the general formula III, one may use, for example:

1-phenylpiperazine, 1-(o-, m- or p-tolyl) piperazine, 1-(2-, 3- or 4-(ethyl-, propyl-, isopropyl-, butyl-, isobutyl-, sec.-butyl- or tert.-butyl)-phenyl)-piperazine, 1-(2-, 3- or 4-(methoxy-, ethoxy-, propoxy-, isopropoxy-, butoxy-, isobutoxy-, sec.-butoxy- or tert.-butoxy)-phenyl) piperazine, 1-(2-, 3- or 4-(methylmercapto-, ethylmercapto-, propylmercapto-, isopropylmercapto-, butylmercapto-, isobutylmercapto-, sec.-butylmercapto-, or tert.-butyl-mercapto)-phenyl) piperazine, 1-(2-, 3- or 4-trifluoro methylphenyl)-piperazine, 1-(2-, 3- or 4-(fluoro-, chloro- or bromo)-phenyl) piperazine, 1-phenyl-(2 or 3)-methylpiperazine, 1-phenyl-(2 or 3)-ethylpiperazine, 1-phenyl-(2 or 3)-propylpiperazine, or 1-phenyl-(2 or 3)-butylpiperazine, and also 1-(o-, m- or p-tolyl)-2-methylpiperazine, 1-(o-, m- or p-tolyl)-3-propylpiperazine, 1-(2-ethylphenyl)-3-butylpiperazine, 1-(3-propylphenyl)-2-isopropylpiperazine, 1-(2-methoxyphenyl)-(2 or 3)-methylpiperazine, 1-(2-, 3- or 4-ethylmercaptophenyl)-3-ethylpiperazine, 1-(2-trifluoromethyl-phenyl)-3-isobutylpiperazine or 1-(2-, 3- or 4-chlorophenyl)-2-methylpiperazine.

Particularly preferred are aryl piperazines of the formula III*, for example, 1-(o-, m- or p-tolyl)-piperazine, 1-(3- or 4-methoxyphenyl)-piperazine, 1-(2-, 3- or 4-(ethoxy-, propoxy-, isopropoxy-, butoxy-, isobutoxy-, sec.-butoxy- or tert.-butoxy)-phenyl)-piperazine or 1-(2-, 3- or 4-(fluoro or chloro)-phenyl) piperazine, especially 1-2-methoxyphenyl)-piperazine.

The intramolecular condensation according to the second stage of the process (a) takes place either by heating a compound of the general formula IV, preferably to 100° to 120° C, with strongly basic agents, such as alkali hydroxides, alkali alcoholates, tetra-alkyl ammonium hydroxides, or with an excess of the aryl piperazine used in the first stage of the process according to (a). If desired an organic solvent, such as, ethyleneglycol monomethyl ether, monoethyl ether or dimethylformamide, may be used. The condensation can also be carried out by heating the compound to a temperature above the melting point, preferably to temperatures between 150° and 250° C, either in vacuo or in a high-boiling inert organic liquid, such as, diphenylmethane or diphenylether.

The replacement of the halogen atom of a compound of the general formula V by an aryl piperazine of the general formula III according to the process (b) is preferably carried out under the conditions stated for the first stage of process (a).

As ω-halogenalkyl quinazolones of the general formula V, one can use, for example, the following:

2-(chloro-, bromo- or iodo-methyl)-4-(3H)-quinazolone, 2-(1- or 2-(chloro- or bromo)-ethyl)-4(3H)-quinazolone, 2-(1-, 2- or 3-(chloro- or bromo)-propyl)-4-(3H)-quinazolone, 2-(1-, 2-, 3- or 4-(chloro or bromo)-butyl)-4-(3H)-quinazolone, 2-(1-, 2-, 3-, 4- or 5-(chloro- or bromo)-pentyl-4-(3H)-quinazolone, 2-(1-, 2-, 3-, 4-, 5- or 6-(chloro- or bromo)-hexyl)-4-(3H)-quinazolone, 2-(1- or 2-methyl-3-chlorpropyl)-4(3H)-quinazolone, 2-(1- or 2-ethyl-3-chloropropyl)-4(3H)-quinazolone, 2-(3-(chloro- or bromo)-propen-(1)-yl)-4(3H)-quinazolone or the 6- or 7-(methyl-, ethyl-, propyl-, isopropyl-, butyl-, tert.-butyl- or hexyl)-, the 6,7- or 7,8-dimethyl-, the 6-methyl-7-propyl-, the 6,7,8-trimethyl-, the 6- or 7-(chloro- or bromo)-, the 6- or 7-(methoxy-, ethoxy-, propoxy-, isopropoxy-, butoxy-, isobutoxy-, sec.-butoxy-, tert.-butoxy- or allyloxy-, the 6,7- or 7,8-(dimethoxy- or diethoxy)- or the 6,7,8-trimethoxy-4(3H)-quinazolones with the radicals mentioned in position 2 of the above compounds, or the 6- or 7-(methyl-, ethyl-, propyl-, isopropyl-, tert.-butyl- or hexyl)-, the 6,7- or 7,8-dimethyl-, the 6-methyl-7-propyl-, the 6,7,8-trimethyl-, the 6- or 7-(chloro- or bromo)-, the 6- or 7-(methoxy-, ethoxy-, propoxy-, isopropoxy, butoxy-, isobutoxy-, sec.-butoxy-, tert.-butoxy- or allyloxy-, the 6,7- or 7,8-(dimethoxy- or diethoxy)- or the 6,7,8-trimethoxy-3-(methyl-, ethyl-, propyl-, isopropyl-, butyl-, pentyl-, isopentyl-, benzyl-, β-phenylethyl-, cyclopropyl-, cyclopentyl- or cyclohexyl)-4-(3H)-quinazolones with the radicals mentioned in position 2 of the above compounds.

Particularly preferred are ω-halogenalkyl quinazolones of the general formula V*, for example, 2-(2-chloro- or bromo)-ethyl- or 3-(chloro- or bromo)-propyl)-6- or 7-(methyl-, ethyl-, methoxy- or ethoxy)-4(3H)-quinazolones, 2-(2-(chloro- or bromo)-ethyl- or 3-(chloro- or bromo)-propyl)-3-(methyl- or ethyl)-6- or 7-(methyl-, ethyl-, methoxy- or ethoxy)-4(3H)-quinazolones, 2-(2-(chloro- or bromo)-ethyl- or 3-(chloro- or bromo)-propyl)-6,7- or 7,8-(dimethyl-, dimethoxy- or diethoxy)-4(3H)-quinazolones or 2-(2-chloro- or bromo)-ethyl- or 3-(chloro- or bromo)-propyl)-3-(methyl- or ethyl)-6,7- or 7,8-(dimethyl-, dimethoxy- or diethoxy)-4(3H)-quinazolones.

The condensation according to the process (c) is carried out by heating the initial substances to temperatures between 60° and 180° C. The temperature is preferably 120° to 180° C when using amides or nitriles and 60° to 120° C when using imide acid esters or amidines. The heating may be carried out in a solvent, for example, a low-molecular alcohol preferably at its boiling point.

Anthranilic acids of the general formula VI which can be used are, for example, anthranilic acid; 4- or 5-monoalkylanthranilic acids, such as, for example, 4- or 5-(methyl-, ethyl-, propyl-, isopropyl-, butyl-, isobutyl-, sec.-butyl-, tert.-butyl-, pentyl-, isopentyl-, hexyl-, allyl-, propen-1-yl- or buten-2-yl)-anthranilic acid; 3,4- or 4,5-dialkylanthranilic acids, such as, for example, 3,4- or 4,5-(dimethyl-, diethyl-, dipropyl-, ethylmethyl- or butylmethyl)-anthranilic acid; 3,4,5-trialkylanthranilic acids, such as, for example, 3,4,5-trimethyl- or tirethylanthranilic acid, 4- or 5-halogen-anthranilic acids, especially 4- or 5-chloroanthranilic acid or 4- or 5-bromo-anthranilic acid; 4- or 5-(methoxy-, ethoxy-, propoxy-, isopropoxy-, butoxy-, isobutoxy-, sec.-butoxy-, tert.-butoxy, pentyloxy-, isopentyloxy-, hexyloxy-, allyloxy-, buten-2-yl-oxy- or 2-methylallyloxy)-anthranilic acid; 3,4- or 4,5-dialkoxyanthranilic acids, such as, for example, 3,4- or 4,5-(dimethoxy-, diethoxy-, dipropoxy-, ethoxy-hexyloxy-, butoxy-methoxy- or methoxy-isopropyl)-anthranilic acid; or 3,4,5-trialkoxyanthranilic acids, such as, for example, 3,4,5-trimethoxy- or triethoxy-anthranilic acid.

Preferred are anthranilic acids of the general formula VI*, for example, 4- or 5-(methyl-, ethyl-, methoxy- or ethoxy)-anthranilic acid or 3,4- or 4,5-(dimethyl-, diethyl-, dimethoxy- or diethoxy)-anthranilic acid. A reactive ester of a compound of the general formula VI or VI* is, for example, the ester of a lower alkanol with 1 to 4 carbon atoms, especially the methyl- or ethyl-ester, of one of the above-mentioned anthranilic acids. (4-aryl-piperazinyl-(1))-carboxylamides, nitriles, amidines and iminoesters of the general formulae VII, VIII or IX are, for example, 4-aryl-piperazinyl-(1)-acetamide, -acetonitrile, -acetamidine or -acetaiminoethyl ester, 2- or 3-(4-aryl-piperazinyl-(1))-propionamide, -propionitrile, -propionamidine or -propionic acid iminomethyl- or ethyl ester, 2-, 3- or 4-(4-aryl-piperazinyl-(1))-butyramide, -butyronitrile, -butyramidine or -butyric acid iminomethyl- or ethyl ester, 2-, 3-, 4- or 5-(4-aryl-piperazinyl-(1))-valero-amide, -valeronitrile, -valeroamidine or -valeric acid iminomethyl ester, 2-, 3-, 4-, 5- or 6-(4-aryl-piperazinyl-(1))-caproamide, -capronitrile, -caproamidine, or -caproic acid iminoethyl ester, 2-, 3-, 4-, 5-, 6- or 7-(4-aryl-piperazinyl)-(1))-oenanthamide, -oenanthonitrile, -oenenthamidine or or oenanthic acid iminomethyl ester, 2-methyl-3-(4-arylpiperazinyl-(1))-butyramide, -butyronitrile, -butyramidine or -butyric acid iminomethyl ester or 4-(4-aryl-piperazinyl-(1))-crotonamide, -crotonitrile, -crotonamidine or -crotonic acid iminomethyl- or ethyl ester, in which the aryl piperazinyl radical represents the radical of one of the aryl piperazines mentioned above for formula III.

Preferably the reaction is carried out with compounds of the formulae VII*, VIII* or IX*, for example, 3-(4aryl piperazinyl-(1)-propionamide, -propionitrile, -propionamidine, -propionic acid iminomethyl- or ethyl ester and 4-(4-aryl-piperazinyl-(1))-butyramide, -butyronitrile, -butyramidine, -butyric acid iminomethyl- or ethyl ester, in which the aryl piperazinyl radical represents the radical of one of the aryl piperazines mentioned above for formula III*.

The production of salts of non-toxic inorganic and organic acids can usually be carried out by dissolving the free bases and adding the requisite quantity of acid. Examples of inorganic acids which may be considered are: hydrogen halide acids, such as, hydrochloric acid or hydrobromic acid, also sulphuric acid, phosphoric acid or sulphamidic acid. By way of example one may mention as organic acids: acetic acid, propionic acid, lactic acid, glycolic acid, gluconic acid, oxalic acid, maleic acid, fumaric acid, succinic acid, tartaric acid, citric acid, acetylglycine, benzoic acid, salicylic acid, pamoic acid, methanesulphonic acid, oxethanesulphonic acid, polygalacturonic acid, polyvinylcarboxylic acid or ethylenediamine tetracetic acid. The salts of the compounds according to the invention can be readily soluble or sparingly soluble in water, the sparingly soluble salts being used particularly for the production of delayed-action forms of the compounds according to the invention.

Surprisingly the compounds according to the invention of general formula I possess only slight sedative properties and no anticonvulsive properties, but pronounced hypotensive, antihistaminic and analgesic properties. The following tables I to V show the extent of these activities as well as details of toxicity and compare them with the effects of known substances. Substances used for comparison were: phentolamine, chlorodiazepoxide, Meprobamate, aminophenazone, morphine hydrochloride, and piprine hydrate = (1-methyl-piperidyl-4)-benzhydryl ether-8-chlorotheophyllinate.

Table I

Influence on the blood pressure and cardiac frequency and also on the carotid sinus reflex of the narcotised cat

| Example No. | Blood pressure lowered by | | Cardiac frequency | | Inhibition of the carotid sinus reflex by | |
|---|---|---|---|---|---|---|
| | 30% by | 50% by | lowered | raised | 30% by | 50% by |
| 2 | 0.029 | >1.6 | + | − | <0.01 | 0.02 |

Table I-continued

Influence on the blood pressure and cardiac frequency and also on the carotid sinus reflex of the narcotised cat

| Example No. | Blood pressure lowered by 30% by | Blood pressure lowered by 50% by | Cardiac frequency lowered | Cardiac frequency raised | Inhibition of the carotid sinus reflex by 30% by | Inhibition of the carotid sinus reflex by 50% by |
|---|---|---|---|---|---|---|
| 6 | 0.07 | 0.61 | + | − | 0.12 | 0.35 |
| 10 | 0.03 | 1.4 | + | − | <0.02 | 0.03 |
| 11 | 0.04 | >1.6 | + | − | 0.017 | 0.04 |
| 14 | 0.9 | >1.6 | ± | ± | 0.04 | 0.15 |
| 17 | 4.5 | >1.5 | + | − | — | — |
| Phentolamine | 0.1 | 0.7 | − | + | 0.1 | 0.5 |

Table I provides a general summary of the influence of different piperazinylquinazolones on the blood pressure, the cardiac frequency and the carotid sinus reflex of the narcotised cat.

Table II

Influence on the blood pressure and the cardiac frequency of the narcotised rat and also on the hypertensive effect of 0.001 mg/kg i/v 1-adrenalin and noradrenalin on the despinalised rat

| Example | $LD_{50}$ (mean lethal dose) on the mouse | Narcotised rat Blood pressure lowered by 30% by mg/kg i/v | Narcotised rat Cardiac frequency lowered | Narcotised rat Cardiac frequency increase | Despinalised rat 50% inhibition of hypertensive effect after i/v dose of Adrenalin by mg/kg i/v | Despinalised rat 50% inhibition of hypertensive effect after i/v dose of Noradrenalin by mg/kg i/v |
|---|---|---|---|---|---|---|
| 1 | 70 | 0.3 | + | − | 0.23 | 5.0 |
| 2 | 70 | 0.65 | − | − | 0.042 | 1.4 |
| 3 | 200 | 0.32 | − | − | 0.35 | 5.0 |
| 4 | 100 | 0.65 | + | − | — | — |
| 6 | 600 | 0.35 | + | − | 0.036 | >2.5 |
| 8 | 350 | 0.12 | + | − | 0.035 | — |
| 10 | 300 | 0.4 | + | − | 0.0085 | 1.8 |
| 11 | 200 | 0.1 | + | − | 0.048 | >2.5 |
| 14 | 150 | 0.18 | + | − | 0.058 | >2.5 |
| 15 | 200 | 0.2 | + | − | 0.32 | 4.3 |
| 16 | 300 | 0.6 | + | − | 0.57 | 4.0 |
| 20 | 300 | 0.65 | + | − | 0.05 | 1.15 |
| Phentolamine | 200 | 0.63 | − | − | 0.047 | 0.18 |

Table II shows the influence of various piperazinyl quinazolones on the blood pressure and the cardiac frequency of the narcosed rate and also on the hypertensive effect of 0.001 mg/kg i.v. 1-adrenaline and noradrenaline on the despinalised rat. The mean lethal doses for the mouse are also given.

From Tables I and II it can be seen that the piperazinyl quinazolones according to the invention generally have a stronger hypotensive action and a lower toxicity than phentolamine which in the blood vessels specifically inhibits the stimulating action of noradrenaline and adrenaline.

The inhibition of the carotid sinus reflex brought about by the piperazinyl quinazolones occurs at lower doses than the spontaneous lowering of the blood pressure in the cat. This shows that the compounds according to the invention inhibit central hypertensive mechanisms of the circulation.

The central damping actions of the piperazinyl quinazolones on the mouse can be seen from Table III. A comparison between the doses which influence the circulation and those which have a central damping effect shows that the influence on the circulation takes place preferentially, which means to say that the hypotensive doses are below those which reduce the motor behaviour, that is to say the normal movement operation.

Key to Table III:
a = dose at which 50% of the mice fall from a rotating bar;
b = dose at which an average of 50% of the mice display the following symptoms: inhibition of spontaneous motility, sedation, muscular relaxation, loss of power to grip and hold themselves on a horizontal wire mesh;
c = average percentage inhibition of the running activity of mice which had been pre-treated with 5 mg/kg. of α-amphetamine sulphate (reckoned on the activity of mice which had only received α-amphetamine sulphate) over a period of 180 minutes;
d = percentage prolongation of the duration of sleep of mice which had received 75 mg/kg. of hexobarbital, reckoned on the duration of the sleep of control animals.

Table III

| Example No. | a $PD_{50}$ mg/kg i.p. | b $SD_{50}$ mg/kg oral | Central effects on the mouse c % inhibition of motility in the treadwheel by 12mg/kg i/p | Central effects on the mouse c % inhibition of motility in the treadwheel by 25mg/kg i/p | d % prolongation of sleep under hexobarbital by 15 mg/kg i.p. |
|---|---|---|---|---|---|
| 1 | 33 | 1000 | 15 | 55 | 64 |
| 2 | 35 | 140 | 11 | 10 | 121 |
| 3 | 24 | 60 | 13 | 41 | 69 |
| 4 | 23 | 70 | 51 | 65 | 125 |
| 6 | 34 | 40 | 19 | 28 | 79 |
| 11 | 53 | 110 | 18 | 32 | 87 |

Table III-continued

| | | Central effects on the mouse | | |
|---|---|---|---|---|
| | a | b | c | d |
| | | | % inhibition of motility in the treadwheel by | % prolongation of sleep under hexebarbital by |
| Example No. | PD$_{50}$mg/kg i.p. | SD$_{50}$mg/kg oral | 12mg/kg i/p / 25mg/kg i/p | 15 mg/kg i.p. |
| 12 | 34 | 500 | 0 / 19 | 78 |
| 13 | 46 | 200 | +15 / +15 | 44 |
| 14 | 61 | 180 | +16 / 1 | 68 |
| 16 | 14 | 65 | 10 / 49 | 103 |
| 18 | | 1000 | +22 / +12 | ±>15 |
| Chlordiazepoxide | 38 | 8 | +15 / 19 | 324 |
| Meprobamate | 95 | 300 | +11 / +28 | 18 |

From Table IV below one can see the analgesic action, measured in terms of the delayed reaction during the thermal irritation of the mouse tail. The analgesically effective doses are also below those which reduce the motor behaviour, that is to say the normal movement processes (cf. Table III).

Table IV

| | Analgesic effect on the mouse |
|---|---|
| | Delay in the defence reaction after the thermal stimulation of the tail of the mouse by 25% by |
| Example No. | mg/kg per os |
| 1 | 1.5 |
| 2 | 1 |
| 3 | 2 |
| 4 | 3 |
| 5 | <1 |
| 6 | 1.5 |
| 7 | 1 |
| 8 | 10 |
| 10 | 2 |
| 11 | 4 |
| 12 | 1.5 |
| 13 | 2 |
| 14 | 2 |
| 15 | 1 |
| 16 | 2.5 |
| 17 | 2 |
| 18 | 8 |
| 20 | 2 |
| Aminophenazone | 80 |
| Morphine hydrochloride | 2 |

Another surprising feature is the strong antihistamine activity of the piperazinylquinazolones according to the invention:

Table V

| | Antihistaminic action |
|---|---|
| | 50% inhibition of the histamine spasm of the isolated guinea pig small intestine by |
| Example No. | g/ml. |
| 1 | 3.5 × 10$^{-9}$ |
| 2 | 6.5 × 10$^{-9}$ |
| 3 | 1.5 × 10$^{-9}$ |
| 4 | 8 × 10$^{-9}$ |
| 6 | 3 × 10$^{-9}$ |
| 7 | 2 × 10$^{-9}$ |
| 11 | 3 × 10$^{-9}$ |
| 12 | 3.5 × 10$^{-10}$ |
| 13 | 2.5 × 10$^{-9}$ |
| 15 | 7 × 10$^{-9}$ |
| 16 | 3.5 × 10$^{-9}$ |
| 20 | 2.5 × 10$^{-9}$ |
| Piprine hydrinate | 1.5 × 10$^{-8}$ |

An orientating clinical test which was carried out with the compound of Example 6 on 7 female and 1 male patient with doses of 10 and 20 mg per os, showed a very good tolerance, no effect on the sensorium and a statistically significant lowering of the systolic and diastolic blood pressure.

Figure 2:
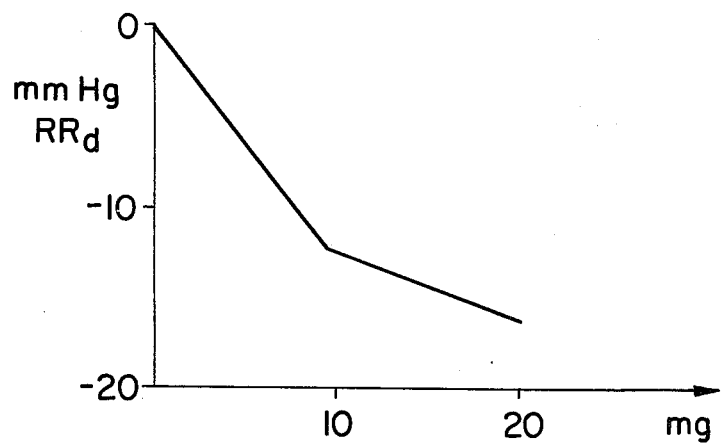

FIGS. 1 and 2 show the variations in the blood pressure at various doses of 2-(2-(1(-2-methoxyphenyl) piperazinyl-4) ethyl)-6,7-dimethoxy-(4(3H)-quinazolone in relation to the mean initial blood pressure of 171.9 mm Hg systolic and 95.3 mm Hg diastolic; FIG. 1 is based on the mean initial blood pressure of 171.9 mm Hg systolic and FIG. 2 is based on the mean initial blood pressure of 95.3 mm Hg diastolic. The lowering of the blood pressure is therefore seen to be dependent upon the dose. The difference in the action of 10 and 20 mg. is statistically confirmed.

From the pharmacological and clinical investigations it can be seen that the piperazinyl quinazolones of the general formula I and their salts of pharmcologically tolerable inorganic or organic acids are valuable therapeutic aids, particularly for the treatment of high blood pressure.

Pharmaceutical products can be prepared which contain one or more of the compounds according to the invention in the form of the free bases or of a pharmacologically tolerable acid addition salt as active principle, possibly also in admixture with other pharmacologically active substances. These pharmaceutical products can be produced in the usual manner by combining the active principle with a pharmaceutical support, such as a filler, a diluent, a corrective and/or other usual ingredients for pharmaceutical products. The products can be produced in the solid state in the form of tablets or capsules or in the liquid state in the form of solutions or suspensions. In the case of administration by intravenous route three times a day the individual dose is from 1 to 50 mg, preferably 5 to 20 mg. For administration three times a day by intramuscular route the individual dose is 1 to 50 mg., preferably 10 to 25 mg. When administered per os three times a day, the individual dose is from 1 to 100 mg., preferably 5 to 60 mg. The pharmaceutical products according to the invention can also be adminisered in other ways, for example by intraperitoneal or subcutaneous route. The pharmaceutical support can also contain the usual diluents or tabletting additives, such as cellulose powder, corn starch, lactose and talcum, just as are usual for such purposes.

The invention therefore also relates to pharmaceutical products, especially for the treatment of high blood pressure, which are characterised by their containing one or more compounds of the general formula I.

EXAMPLE OF A BATCH FOR THE PRODUCTION OF 75,000 TABLETS CONTAINING 20 MG. OF ACTIVE PRINCIPLE OF EXAMPLE 6

Ingredients:

```
1.500 kg. compound of Example 6
6.000 kg. corn starch
4.875 kg. lactose
0.225 kg. amorphous silica
0.300 kg. sodium lauryl sulphate
0.375 kg. polyvinylpyrrolidone
1.200 kg. pectin
0.375 kg. talcum
0.150 kg. magnesium stearate
15.000 kg.
```

The active principle, the corn starch, the lactose, the amorphous silica and the sodium lauryl sulphate are mixed and sieved. This mixture is moistened with a solution of the polyvinylpyrrolidone in 2.4 litres of alcohol and granulated through a sieve with a mesh of 1.25 mm. The granulate is dried at 40° C and mixed with the pectin, talcum and magnesium stearate. This mixture is pressed on the rotary press into tablets of 200 mg. and a diameter of 8 mm.

EXAMPLE OF A BATCH FOR THE PRODUCTION OF 200,000 CAPSULES CONTAINING 20 MG. ACTIVE PRINCIPLE

Ingredients:

```
4.000 kg. compound of Example 6
15.990 kg. microcrystalline cellulose
0.010 kg. amorphous silica
20.000 kg.
```

The compound of Example 6 in the finely powdered form, the microcrystalline cellulose and the unpressed amorphous silica are thoroughly mixed and filled into hard gelatin capsules of size 4.

The invention also relates to halogenalkanoic acid-6-carbamyl anilides of the general formula II

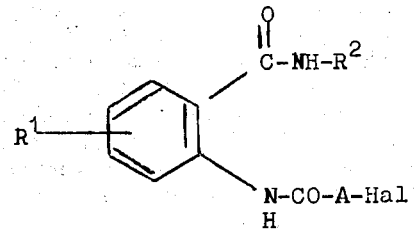

II in which $R^1$, $R^2$, A and Hal have the meanings given above.

Those preferred are halogenalkanoic acid-6-carbamyl anilides of the general formula II*

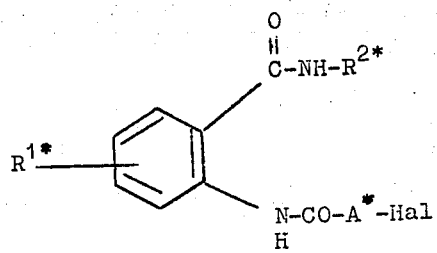

II* in which $R^{1*}$, $R^{2*}$, A* and Hal have the meanings given above.

The halogenalkanoic acid-6-carbamyl anilides of the general formula II, especially II*, can be used as initial compounds for the production of aryl-substituted piperazinyl alkyl quinazolone-(4) derivatives according to the invention and having the general formula I, especially I*, and therefore constitute valuable chemical intermediates.

Finally the invention reltes to a process for the production of halogenalkanoic acid-6-carbamyl anilides of the general formula II $$\begin{array}{c} \phantom{R^1-} \overset{O}{\underset{\|}{C}}-NH-R^2 \\ R^1- \phantom{XXX} \\ \phantom{R^1-}\underset{H}{N}-CO-A-Hal \end{array}$$

II in which $R^1$, $R^2$, A and Hal have the meanings given above; the process is characterised by the fact that 6-carbamyl anilines of the general formula X:

$$\begin{array}{c} \phantom{R^1-}\overset{O}{\underset{\|}{C}}-NHR^2 \\ R^1- \phantom{XXX} \\ \phantom{R^1-XXX}NH_2 \end{array}$$

X in which $R^1$ and $R^2$ have the meanings given above, are reacted with halogenalkanoic acid halides of the general formula XI

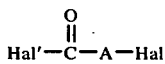

in which Hal and A have the meanings given above and Hal' signifies a chlorine or bromine atom, or halogenalkanoic acid anhydrides of the general formula XII

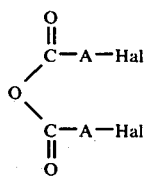

in which A and Hal have the meanings given above, in the presence of one or more inorganic and/or organic auxiliary bases in an inert organic solvent.

In the process for the production of halogenalkanoic acid-6-carbamyl anilides of the general formula II or II* one uses as inorganic auxiliary bases alkali or alkali earth carbonates, especially sodium carbonate or potassium carbonate, or alkali bicarbonates, especially sodium bicarbonate; preferred auxiliary organic bases are tertiary amines, for example triethylamine, ethyldiisopropylamine, and pyridine. As organic auxiliary bases it is also possible to use an excess of 6-carbamyl aniline of the general formula II or II*. As inert solvent one uses preferably hydrocarbons, for example, benzene, toluene or xylene, halogenated hydrocarbons, for example, methylene chloride, chloroform, trichlorethylene, chlorobenzene or o-dichlorobenzene, or ethers, for example di-isopropyl ether, tetrahydrofuran or dioxan, or mixtures of the above-mentioned solvents.

The reaction temperatures are not critical; they are generally within the range from 0° to 80° C, especially 10° to 30° C.

In order to obtain good yields one proceeds as follows in a particularly preferred form of execution of the process of the invention for the production of halogenalkanoic acid-6-carbamyl anilides of the general formula II or II*:

The 6-carbamyl aniline is placed in one of the above-mentioned solvents. Per mole of 6-carbamyl aniline one adds 0.5 moles of halogenalkanoic acid halide or anhydride, dissolved in one of the solvents listed above, accompanied by stirring and if necessary by cooling. To the resultant reaction mixture one adds, per mole of 6-carbamyl aniline used, 0.5 moles of organic auxiliary base, accompanied by stirring. One adds further halogenalkanoic acid halide or anhydride, namely 0.25 moles per mole of 6-carbamyl aniline used, that is to say one-half of the quantity previously added. This is followed once again by the addition of 0.25 moles of organic auxiliary base per mole of 6-carbamyl aniline used, that is to say one-half of the quantity previously added. This alternating addition of half the quantities of halogenalkanoic acid halide or anhydride and half the quantities of organic auxiliary base is repeated again several times. The isolation of the halogenalkanoic acid-6-carbamyl aniliden of the general formula II or II* is carried out in the usual manner, for example by the addition of dilute acid followed by filtration or extraction.

The 6-carbamyl anilines used as initial compounds in the process according to the invention for the production of halogenalkanoic acid-6-carbamyl anilines can be produced by the catalytic reduction of o-nitrobenzoic acid amides of the general formula XIII

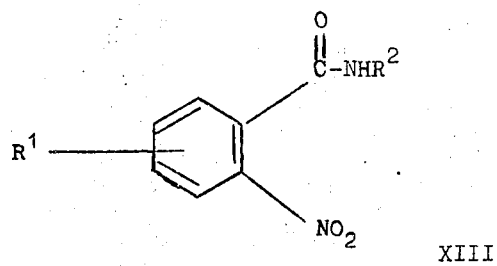

in which $R^1$ and $R^2$ have the meanings given above. The o-nitrobenzoic acid amides can in turn be obtained by reacting the corresponding o-nitrobenzoic acid chlorides with primary amines or ammonia.

The examples are intended to illustrate the invention in greater detail without restricting same.

Table VI

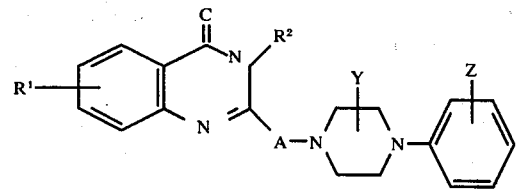

| Example No. | $R^1$ | $R^2$ | A | Y | Z | M.P. °C | crystallised from | Yield % of theory |
|---|---|---|---|---|---|---|---|---|
| 1 | 6.7-di-OCH₃ | H | —CH₂—CH₂— | H | H | 214–215 | Ethyl acetate | 78 |
| 2 | 6.7-di-OCH₃ | H | —CH₂—CH₂— | H | 2-CH₃ | 204–205 | Ethyl acetate | 64 |
| 3 | 6.7-di-OCH₃ | H | —CH₂—CH₂— | H | 3-CH₃ | 212–213 | Ethyl acetate | 86 |
| 4 | 6.7-di-OCH₃ | H | —CH₂—CH₂— | H | 4-CH₃ | 232–233 | Ethyl acetate | 52 |
| 5 | 6.7-di-OCH₃ | H | —CH₂—CH₂— | H | 3-CH₃ | 239–240 | Ethyl acetate | 74 |
| 6 | 6.7-di-OCH₃ | H | —CH₂—CH₂— | H | 2-OCH₃ | 214–215 | Ethyl alcohol | 75 |
| 7 | 6.7-di-OCH₃ | H | —CH₂—CH₂— | H | 3-OCH₃ | 194–196 | Ethyl acetate | 57 |
| 8 | 6.7-di-OCH₃ | CH₃ | —CH₂—CH₂— | H | 2-OCH₃ | 211–212 | Ethyl acetate | 46 |
| 9 | 6.7-di-OCH₃ | —CH₂.CH₂—C₆H₃ | —CH₂—CH₂— | H | 2-OCH₃ | 162–163 | Ethyl acetate | 42 |
| 10 | 6.7-di-OCH₃ | H | —CH₂—CH₂— | H | 2-OC₂H₅ | 207–208 | Ethanol | 62 |
| 11 | 6.7-di-OCH₃ | H | —CH₂—CH₂— | H | 2-Cl | 226–227 | Ethyl acetate | 81 |
| 12 | 6.7-di-OCH₃ | H | —CH₂—CH₂— | H | 3-Cl | 224–225 | Ethyl acetate | 60 |
| 13 | 6.7-di-OCH₃ | H | —CH₂—CH₂— | H | 4-Cl | 231–232 | Ethyl acetate | 68 |
| 14 | 6.7-di-OCH₃ | H | —CH₂—CH₂— | H | 2-F | 210 | Ethyl acetate | 56 |
| 15 | 6.7-di-OCH₃ | H | —CH₂—CH₂— | H | 3-F | 221 | Ethyl acetate | 64 |
| 16 | 6.7-di-OCH₃ | H | —CH₂—CH₂— | H | 4-F | 250–251 | Ethyl acetate | 45 |

Table VI-continued

| Example No. | R¹ | R² | A | Y | Z | M.P. °C | crystallised from | Yield % of theory |
|---|---|---|---|---|---|---|---|---|
| 17 | 6.7-di-OCH₃ | H | —CH₂—CH₂— | H | 4-OCH₃ | 218 | Ethanol | 52 |
| 18 | 6.7-di-OCH₃ | H | —CH₂— | H | 2-OCH₃ | 210 | Ethyl acetate | 83 |
| 19 | H | H | —CH(C₂H₅)— | H | 2-OCH₃ | 180–181 | Ethyl acetate/ Methanol 9:1 | 83.5 |
| 20 | 6.7-di-OCH₃ | H | —CH₂—CH₂—CH₂— | H | 2-OCH₃ | 175–176 | Methanol | 59 |
| 21 | 6.7-di-OCH₃ | Cyclohexyl | —CH₂—CH₂—CH₂— | H | 2-OCH₃ | 214–216 | Ethyl acetate | 22.5 |
| 22 | 6.7-di-OCH₃ | —CH₂—CH₂—CH(CH₃)₂ | —CH₂— | H | 2-OCH₃ | 147 | Ethyl acetate/ Cycloh. 3:7 | 37 |
| 23 | 6.7.8-tri-OCH₃ | H | —CH₂—CH₂— | H | 2-OCH₃ | 164 | Ethyl acetate | 82 |
| 24 | 6.7.8-tri-OCH₃ | H | —CH₂—CH₂— | H | 2-Cl | 172 | Ethyl acetate | 85 |
| 25 | 6-CH₃ | H | —CH=CH—CH₂— | H | 2-OCH₃ | 169–170 | Ethyl acetate | 95 |

EXAMPLE 1

2-(2-(1-phenylpiperazinyl-4)ethyl)-6,7-dimethoxy-4(3H)-quinazolone

To a solution of 14.2 g (0.04 moles) of 3-bromopropionic acid-(3,4-dimethoxy-6-carbamyl) anilide in 100 mls. of acetonitrile heated to 50° C one adds a mixture of 7 g (0.04 moles) of 1-phenylpiperazine and 7.8 g (0.04 moles) of dicyclohexylamine in 50 mls. of ethyl alcohol. The crystal paste which is immediately formed is stirred for about 5 hours at 50° to 70° C and then freed from solvents in vacuo. The residue is taken up in 100 mls. of hot chloroform, separated from the undissolved residue and the clear solution is concentrated by evaporation in vacuo. The oily product is dissolved in 100 mls. of ethyleneglycol monoethyl ether, 2.24 g (0.04 moles) of solid potassium hydroxide are added and the mixture is heated to 100° C for 10 to 15 minutes. The vigorously stirred solution is poured into 500 mls. of iced water which contains 3 g of ammonium chloride and semi-concentrated aqueous ammonia is added until the reaction is alkaline. The precipitate is filtered at the pump, washed thoroughly with water and dried. After re-crystallisation from ethyl acetate, one obtains 15 g (78% of theory) of 2-(2-(1-phenyl-piperazinyl-4)ethyl)-6,7-dimethoxy-4(3H)-quinazolone with a melting point of 214°–215° C.

In the same way as described in Example 1, the following compounds are produced by using the corresponding initial material:

EXAMPLE 2

2-(2-(1-(2-tolyl)-piperazinyl-4)ethyl)-6,7-dimethoxy-4(3H)-quinazolone in a yield of 64% and with a melting point of 204°–205° C.

EXAMPLE 3

2-(2-(1-(3-tolyl)piperazinyl-4)ethyl)-6,7-dimethoxy-4(3H)-quinazolone in a yield of 86% and with a melting point of 212°–213° C.

EXAMPLE 4

2-(2-1-(4-tolyl)piperazinyl-4)ethyl)-6,7-dimethoxy-4(3H)-quinazolone in a yield of 52% and with a melting point of 232°–233° C.

EXAMPLE 5

2-(2-(1-(3-trifluoromethylphenyl)piperazinyl-4)ethyl)-6,7-dimethoxy-4(3H)-quinazolone with a yield of 74% and with a melting pont of 239°–240° C.

EXAMPLE 6

2-(2-(1-(2-methoxyphenyl)piperazinyl-4)ethyl)-6,7-dimethoxy-4(3H)-quinazolone in a yield of 75% and with a melting point of 214°–215° C.

EXAMPLE 7

2-(2-(1-(3-methoxyphenyl)piperazinyl-4)ethyl)-6,7-dimethoxy-4(3H)-quinazolone in a yield of 57% and with a melting point of 195°–196° C.

EXAMPLE 8

1-(2-(1-(2-methoxyphenyl)piperazinyl)-4)ethyl)-3-methyl-6,7-dimethoxy-4(3H)-quinazolone in a yield of 46% and with a melting point of 211°–212° C.

EXAMPLE 9

2-(2-(1-(2-methoxyphenyl)piperzinyl-4)ethyl)-3-phenethyl-6,7-dimethoxy-4(3H)-quinazolone in a yield of 42% and with a melting point of 162°–163° C.

EXAMPLE 10

2-(2-(1-(2-ethoxyphenyl)piperazinyl-4)ethyl)-6,7-dimethoxy-4(3H)-quinazolone in a yield of 62% and with a melting point of 207°–208° C.

EXAMPLE 11

2-(2-(1-(2-chlorophenyl)piperazinyl-4)ethyl)-6,7-dimethoxy-4(2H)-quinazolone in a yield of 81% and with a melting point of 226°–227° C.

EXAMPLE 12

2-(2-(1-(3-chlorophenyl)piperazinyl-4)ethyl)-6,7-dimethoxy-4(3H)-quinazolone in a yield of 60% and with a melting point of 224°–225° C.

EXAMPLE 13

2-(2-(1-(4-chlorophenyl)piperazinyl-4)ethyl)-6,7-dimethoxy-4(3H)-quinazolone in a yield of 68% and with a melting point of 231°–232°.

EXAMPLE 14

2-(2-(1-(2-fluorophenyl)piperazinyl-4)ethyl)-6,7-dimethoxy-4(3H)-quinazolone in a yield of 56% and with a melting point of 210° C.

EXAMPLE 15

2-(2-(1-(3-fluorophenyl)piperazinyl-4)ethyl)-6,7-dimethoxy-4(3H)-quinazolone in a yield of 64% and with a melting point of 221° C.

EXAMPLE 16

2-(2-(1(4-fluorophenyl)piperazinyl-4)ethyl)-6,7-dimethoxy-4(3H)-quinazolone in a yield of 45% and with a melting point of 250°–251° C.

EXAMPLE 17

2-(2-(1-(4-methoxyphenyl)piperazinyl-4)ethyl)-6,7-dimethoxy-4(3H)-quinazolone

One dissolves 10 g (0.032 moles) of 3-bromopropionic acid-(3,4-dimethoxy-6-carbamyl)-anilide in 50 mls. of dimethylformamide, adds a solution of 9.1 g (0.036 moles) of 1-(4-methoxyphenyl)piperazine and 7.5 g (0.036 moles) of ethyldicyclohexylamine in 50 mls. of dimethylformamide and the solution is stirred at 80° C for 2 hours. The ethyldicyclohexylamine hydrobromide formed is filtered off at the pump and washed thoroughly with dimethylformamide. The combined filtrates are mixed with 50 mls. of 2N caustic soda solution heated to 100°–110° C for 10 to 15 minutes and finally poured into 500 mls. of ice-cooled ammonium chloride solution. The crystalline precipitate which separates out is filtered off at the pump, thoroughly washed with water and dried in vacuo. The crude product is purified by crystallisation from ethyl alcohol using a hot extractor and in this way one obtains 7.1 g (52% of theory) of 2-(2-(1-(4-methoxyphenyl)piperazinyl-4)ethyl)-6,7-dimethoxy-4(3H)-quinazolone with a melting point of 218° C.

EXAMPLE 18

2-(1-(2-methoxyphenyl)piperazinyl-4)methyl-6,7-dimethoxy-4(3H)-quinazolone

A mixture of 21.0 g (0.077 moles) of chloracetic acid-(3,4-dimethoxy-6-carbamyl)-anilide and 44.3 g (0.23 moles) of 1-(2-methoxyphenyl)piperazine is heated whilst stirring to 110°C. The mass which solidifies after 10 minutes is dissolved in 100 mls. of acetonitrile and stirred for a further 30 minutes at 70° C. The mixture is freed from solvent in vacuo, the residue is taken up in 100 mls. of ethyleneglycolmonomethyl ether which contains 5.6 g of potassium hydroxide, and heated to 100° C for 15 minutes. The solution is poured on to ice, 20 mls. of saturated ammonium chloride solution are added and semi-concentrated aqueous ammonia is added until the reaction becomes slightly alkaline. The precipitate is filtered at the pump, washed with water and dried in vacuo. Any adhering impurities are removed by briefly boiling the crude product with ethyl acetate and then filtering again and drying. In this way one obtains 26.2 g (83% of theory) of 2-(1-(2-methoxyphenyl)piperazinyl-4)-methyl-6,7-dimethoxy-4(3H)-quinazolone with a melting point of 210° C.

EXAMPLE 19

2-($\alpha$-(1-(2-methoxyphenyl)piperazinyl-4)-n-propyl)-4(3H)-quinazolone 19.2 g (0.06 moles) of 2-(2-bromobutyrylamino) benzamide and 35.7 g (0.186 moles) of 1-(2-methoxyphenyl)piperazine are heated to 70° C for 2 hours whilst stirring, and then mixed with a solution of 6.4 g of potassium hydroxide in 70 mls. of glycolmonoethyl ether and then heated to 70° C for a further 30 minutes. The reaction mixture is distributed between saturated ammonium chloride solution and chloroform, the chloroform phase is separated and after drying over calcined potassium carbonate is concentrated by evaporation in vacuo. The oily residue is boiled up with ethyl acetate, allowed to cool slowly and the crystal mass is filtered off at the pump. By redissolving in a 9:1 mixture of ethyl acetate and methyl alcohol it is possible to purify the crude product. In this way one obtains 21.3 g (83.5% of theory) of 2-($\alpha$-(1-2-methoxyphenyl)-piperazinyl-4)-n-propyl)-4(3H)-quinazolone with a melting point of 180°–181° C.

EXAMPLE 20

By using corresponding initial materials, one obtains by the mode of operation stated in Example 19, 2-(3-(1-(2-methoxy-phenyl)-piperazinyl-4)-n-propyl)-6,7-dimethoxy-4(3H)-quinazolone in a yield of 59% and with a melting point of 175°–176° C.

EXAMPLE 21

2-(3-(1-(2-methoxyphenyl)piperazinyl-4)-n-propyl)-3-cyclohexyl-6,7-dimethoxy-4(3H)-quinazolone 10.0 g (0.023 moles) of 4-(bromobutyric acid-(3,4-dimethoxy-6-cyclohexylcarbamyl) anilide and 22.0 g (0.115 moles) of 1-(2-methoxyphenyl) piperazine are stirred at 120° C for 4 hours. The reaction mixture is then poured into 100 mls. of saturated ammonium chloride solution and extracted with chloroform. After drying the chloroform extracts over calcined potassium carbonate, they are concentrated by preparation in vacuo. The residual dark brown oil is purified by column chromatography over neutral silica gel (0.05–0.2 mm) using chloroform as eluent. The eluate is concentrated in vacuo and the residue is heated at 0.5 mm Hg for 2 hours at 160° C. Then the crude product is recrystallised from ethyl acetate. In this way one obtains 2.6 g (22.5% of theory) of 2-(3-(1-(2-methoxyphenyl) piperazinyl-4)-n-propyl)-3-cyclohexyl-6,7-dimethoxy-4(3H)-quinazolone with a melting point of 214°–216° C.

EXAMPLE 22

2-(1-(2-methoxyphenyl) piperazinyl-4) methyl-3-isoamyl-6,7-dimethoxy-4(3H)-quinazolone 4.0 g (0.011 moles) of chloracetic acid-(3,4-dimethoxy-6-isoamylcarbamyl) anilide and 4.3 g (0.022 moles) of 1-(2-methoxyphenyl) piperazine are stirred in 20 mls. of dimethylformamide for 3 hours at 70° C, the solvent is removed for the most part in vacuo, the residue is distributed between 2 N caustic soda solution and chloroform and finally the chloroform phase is purified by column chromatography over 100 g neutral silica gel (0.05–0.2 mm) using chloroform as eluent. The eluate is concentrated in vacuo, the residue is heated in 50 mls. of dimethylformamide with 5 mls. of a 40% solution of benzyltrimethyl ammonium hydroxide in methyl alcohol for 30 minutes at 100° C and the reaction mixture is then poured into 500 mls. of saturated ammonium chloride solution. The oily reaction product is extracted with chloroform. After drying chloroform phase and concentration in vacuo, the reaction product is isolated and made to crystallise with a 3:7 mixture of ethyl acetate and cyclohexane. In this way one obtains 2.0 g (37% of theory) of 2-(1-(2-methoxyphenyl)-piperazinyl-4)-methyl-3-isoamyl-6,7-dimethoxy-4(3H)-quinazolone with a melting point of 147° C.

EXAMPLE 23

By using the corresponding initial compounds, and proceeding analogously to Example 22, one obtains 2-(2-(1-(2-methoxyphenyl)-piperazinyl-4)-ethyl)-6,7,8-trimethoxy-4(3H)-quinazolone with a yield of 82% and a melting point of 164° C.

EXAMPLE 24

By using the corresponding initial compounds, and proceeding analogously to Example 22, one obtains 2-(2-(1-(2-chlorophenyl)-piperazinyl-4)-ethyl)-6,7,8-trimethoxy-4(3H)-quinazolone with a yield of 85% and a melting point of 172° C.

Example 25

2-(3-(1-(2-methoxyphenyl) piperazinyl-4) prop-2-en-1-yl)-6-methyl-4(3H)-quinazolone a. 19.2 g (0.088 moles) of crotonic acid-(2-carbamyl-4-methyl) anilide are heated to 100° C for 15 minutes in a mixture of 30 mls. of ethyl alcohol, 400 mls. of water and 50 mls. of 6N caustic soda solution. The reaction solution is poured with strong agitation into 300 mls. of saturated ammonium chloride solution, the precipitate is filtered at the pump, carefully washed with water and dried in vacuo. After re-dissolving from methyl alcohol one obtains 16.8 g (95% of theory) of 2-propenyl-6-methyl-4(3H)-quinazolone with a melting point of 232°–233° C.

b. 16.0 g (0.08 moles) of N-bromosuccinimide, 14.0 g (0.07 moles) of 2-propenyl-6-methyl-4(3H)-quinazolone and 0.05 g of dibenzoylperoxide in 500 mls. of carbon tetrachloride are boiled under a reflux for 16 hours. The reaction mixture is evaporated to dryness in vacuo and the succinimide is remoed from the residue by boiling out with water several times. The residue which has been purified in this way is then purified by dissolving once again in a 9:1 mixture of methyl alcohol/chloroform and in this way one obtains 8.5 g (38% of theory) of 2-(3-bromopropenyl)-6-methyl-4(3H)-quinazolone with a melting point of 197°–198° C. c. 4.0 g (0.0144 moles) of 2-(3-bromopropenyl)-6-methyl-4(3H)-quinazolone are heated for 5 hours to 80° C with 5.4 g (0.0288 moles) of 1-(2-methoxyphenyl) piperazine in 50 mls. of dimethylformamide. The reaction mixture is then distributed between 10% aqueous ammonia and chloroform and the chloroform phase is evaporated to dryness after drying over calcined potassium carbonate. The residue is purified by crystallisation twice from ethyl acetate. In this way one obtains 5.4 g (96.5% of theory) of 2-(3-(1-(2-methoxyphenyl) piperazinyl-4) prop-2-en-1-yl)-6-methyl-4(3H)-quinazolone with a melting point of 169°–170° C. Using the same mode of operation, when choosing suitable initial materials, one obtains the piperazinylalkyl-4-(3H)-quinazolones described in Examples 1 to 24.

EXAMPLE 26

58.1 g (0.3 moles) of 4,5-dimethoxy-anthranilic acid and 118.35 g (0.45 moles) of 3-(4-(2-methoxyphenyl)-piperazinyl-1)-propionamide are heated to 150° C for 7 hours. After cooling, it is heated with 2N aqueous sodium carbonate solution, extracted with methylene chloride and the methylene chloride solution separated is shaken four times with 0.1 N aqueous sodium hydroxide solution. The caustic soda extract is clarified with active carbon, mixed with hydrochloric acid until the precipitate which is initially formed is redissolved and then rendered alkaline with 2N aqueous sodium carbonate solution, whereby the quinazolone is precipitated. After re-crystallisation from ethyl alcohol one obtains 2-(2-(1-(2-methoxyphenyl)-piperazinyl-4-)-ethyl)-6,7-dimethoxy-4(3H)-quinazolone with a melting point of 214°–215° C. By using the corresponding initial compounds it is possible by means of the process described here to obtain the piperazinylalkyl-4(3H)-quinazolones described in Examples 1 to 7, 10 to 20, 23 and 24.

EXAMPLE 27

40.1 g (0.1 moles) of imino ethyl 3-(4-(2-methoxyphenyl)-piperazinyl-1) propionate trihydrochloride are placed in a mixture of 100 g of 40% aqueous potassium carbonate solution and 100 mls. of ether cooled to −10° C. The ether solution is separated after being shaken, dried with potassium carbonate and the ether distilled off. The oily residue is poured into a hot solution of 22.5 g (0.1 moles) of ethyl 4,5-dimethoxyanthranilate in 100 mls. of ethyl alcohol and heated under a reflux for 1.5 hours. After removing a part of the ethyl alcohol the reaction mixture is poured into water and the precipitated reaction product is purified by hot extraction with ethyl acetate. One obtains 2-(2-(1-(2-methoxyphenyl)-piperazinyl-4) ethyl)-6,7-dimethoxy-4(3H)-quinazolone with a melting point of 214°215° C.

By using the corresponding initial materials and the methods of operation described here one can obtain the piperazinylalkyl-4(3H)-quinazolones described in Examples 1 to 7, 10 to 20, 23 and 24.

Table VII

Precursors and Intermediates

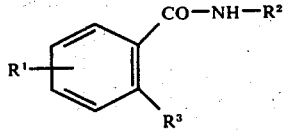

| No. of Example | $R^1$ | $R^2$ | $R^3$ | M.P. °C | crystallised from | Yield % of theory |
|---|---|---|---|---|---|---|
|  | 3,4-di-OCH$_3$ | CH$_3$ | NO$_2$ | 188–189 | Ethyl acetate | 97 |

Table VII-continued

Precursors and Intermediates $$R^1 \underset{R^3}{\overset{CO-NH-R^2}{\diagup\hspace{-0.5em}\diagdown}}$$

| No. of Example | R¹ | R² | R³ | M.P. °C | crystallised from | Yield % of theory |
|---|---|---|---|---|---|---|
| | 3,4-di-OCH₃ | —(CH₂)₂—C₆H₅ | NO₂ | 156–157 | Isopropanol | 74 |
| | 3,4-di-OCH₃ | —(CH₂)₂—CH(CH₃)₂ | NO₂ | 141–142 | Ethyl acetate | 73 |
| | 3,4-di-OCH₃ | Cyclohexyl | NO₂ | 189–190 | Ethyl acetate | 71 |
| | 3,4-di-OCH₃ | CH₃ | NH₂ | 138–139 | Ethyl alcohol | 77 |
| | 3,4-di-OCH₃ | —(CH₂)₂—C₆H₅ | NH₂ | 116–117 | Ethyl acetate | 83 |
| | 3,4-di-OCH₃ | —(CH₂)₂—CH(CH₃)₂ | NH₂ | 98–98.5 | Isopropanol | 68.5 |
| | 3,4-di-OCH₃ | Cyclohexyl | NH₂ | 147–148 | Water | 81.5 |
| 28 | H | H | NH—CO—CH(Br)—CH₂—CH₃ | 146 | Benzene | 72 |
| 29 | 3-CH₃ | H | NH—CO—CH=CH—CH₃ | 211–212 | — | 95 |
| 30 | 3,4-di-OCH₃ | H | NH—CO—CH₂—Cl | 218 | Ethyl acetate | 75 |
| 31 | 3,4-di-OCH₃ | —(CH₂)₂—CH(CH₃)₂ | NH—CO—CH₂—Cl | 142 | Isopropanol/ Cyclohex. 1:1 | 34 |
| 32 | 3,4-di-OCH₃ | H | NH—CO—CH₂—CH₂—Br | 188 | Ethyl acetate | 75 |
| 33 | 3,4-di-OCH₃ | CH₃ | NH—CO—CH₂—CH₂—Br | 150–151 | Ethyl acetate | 71 |
| 34 | 3,4-di-OCH₃ | —(CH₂)₂—C₆H₅ | NH—CO—CH₂—CH₂—Br | 153–154 | Ethyl acetate | 75 |
| 35 | 3,4-di-OCH₃ | H | NH—CO—CH₂—CH₂—CH₂—Cl | 165–166 | Ethyl acetate | 63 |
| 36 | 3,4-di-OCH₃ | Cyclohexyl | NH—CO—CH₂—CH₂—CH₂—Br | 174–175 | Chloroform | 89 |

The initial compounds used in the following Examples 28 to 36 can be produced according to or similarly to the following process:

6-NITROVERATRUMIC ACID-N-METHYLAMIDE

To a solution of 15 g (0.67 moles) of methylamine in 300 mls. of methyl alcohol one adds slowly, whilst stirring and cooling, a solution of 50 g (0.21 moles) of 6-nitroveratrumic chloride (C. A. Fletscher and M. T. Bogert., J. org. Chem. 4, 71 (1939)) in 600 mls. of benzene and the reaction mixture is stirred for 30 minutes at room temperature. The mixture is poured into two liters of iced water, the crystal mass is filtered at the pump and after drying in vacuo is purified if desired by crystallisation from ethyl acetate. In this way one obtains 47.0 g (97% of theory) of 6-nitroveratrumic acid-N-methylamide with a melting point of 188°–189° C.

3,4-dimethoxy-6-aminobenzoic acid-N-methylamide

To a solution of 15.8 g (0.06 moles) of 6-nitroveratrumic acid-N-methylamide in 200 mls. of methyl alcohol boiling under a reflux one adds 15 mls. of an approximately 50% aqueous suspension of Raney nickel and then, while stirring slowly adds drop, by drop 16.1 g (0.3 moles) of hydrazine hydrate. As soon as the reaction which takes place with considerable frothing has ended, the catalyst is filtered off, the filtrate is evaporated to dryness in vacuo and the residue is redissolved in ethyl alcohol. In this way one obtains 10.6 g (76.8% of theory) of 3,4-dimethoxy-6-aminobenzoic acid-N-methylamide with a melting point of 138°–139° C.

EXAMPLE 28

2-bromobutyric acid-(2-carbamyl) anilide

To a solution of 15.0 g (0.11 moles) of anthranilamide in 200 mls. of dioxane there are first of all added drop by drop, accompanied by thorough stirring, a solution of 11.3 g (0.55 moles) of 2-bromobutyryl chloride in 25 mls. of dioxane and then a solution of 5.55 g (0.55 moles) of triethylamine in 25 mls. of dioxane. Into the resultant reaction mixture there is added slowly drop by drop 5.65 g of 2-bromobutyryl chloride in 12.5 mls. of dioxane and then a solution of 2.78 g of triethylamine in 12.5 mls. of dioxane, that is to say one-half quantities of the previously combined reactants. This alternating addition of half quantities of 2-bromobutyryl chloride and half quantities of triethylamine is repeated twice again. After the addition is terminated, the reaction mixture is stirred at room temperature for a further 30 minutes and then freed from most of the solvent in vacuo. The residue is mixed up into a suspension in 0.5 liters of 0.5N hydrochloric acid, filtered at the pump and washed neutral with water and dilute soda solution. After drying in vacuo and crystallisation from benzene, one obtains 24.2 g (72% of theory) of 2-bromobutyric acid-(2-carbamyl)-anilide with a melting point of 146° C. From the benzene solution it is possible to recover a further 6.0 g, the total yield being increased to 90% of theory.

In an analogous manner the following are produced.

EXAMPLE 29

Crotonic aid-(2-carbamyl-4-methyl) anilide in a yield of 95% of theory and with a melting point of 211°–212° C.

EXAMPLE 30

Chloracetic acid-(3,4-dimethoxy-6-carbamyl) anilide in a yield of 75% of theory and with a melting point of 218° C.

EXAMPLE 31

Chloracetic aid-(3,4-dimethoxy-6-(N-isoamylcarbamyl) anilide in a yield of 34% of theory and with a melting point of 142° C.

EXAMPLE 32

3-bromopropionic acid-(3,4-dimethoxy-6-carbamyl) anilide in a yield of 75% of theory and with a melting point of 188° C.

EXAMPLE 33

3-bromopropionic acid-(3,4-dimethoxy-6-(N-methylcarbamyl) anilide in a yield of 71% of theory with a melting point of 150°–151° C.

EXAMPLE 34

3-bromopropionic acid-(3,4-dimethoxy-6-(N-β-phenylethylcarbamyl)) anilide in a yield of 75% of theory and with a melting point of 153°–154° C.

EXAMPLE 35

4-chlorobutyric acid-(3,4-dimethoxy-6-carbamyl-)anilide in a yield of 63% of theory and with a melting point of 165°–166° C.

EXAMPLE 36

4-bromobutyric acid-(3,4-dimethoxy-6-(N-cyclohexylcarbamyl))-anilide in a yield of 89% of theory and with a melting point of 174°–175° C.

We claim:

1. A pharmaceutical composition with blood pressure lowering activity and suitable for the treatment of hypertension, comprising as active ingredient a pharmaceutically effective amount of an aryl-substituted piperazinylalkylquinazolone-(4) derivative of the formula I

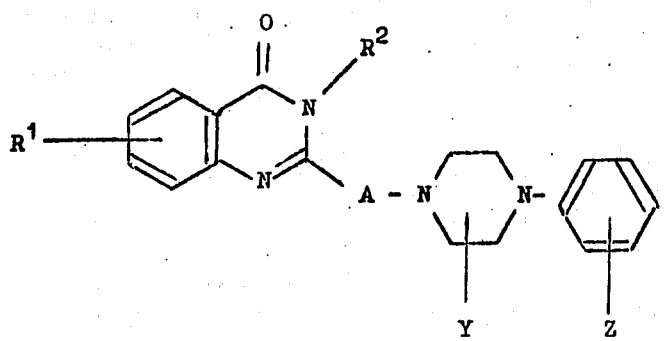

wherein $R^1$ signifies hydrogen, halogen, one to three straight-chained or branched, saturated or unsaturated alkyl groups of 1 to 6 carbon atoms or one to three straight-chained or branched, saturated or unsaturated alkoxy group of 1 to 6 carbon atoms, $R^2$ signifies hydrogen, a straight-chained or branched, saturated or unsaturated alkyl group, a phenylalkyl group or a cycloalkyl group in each case with at the most 6 carbon atoms, A signifies ethylene or trimethylene, Y signifies hydrogen or alkyl of 1 to 4 carbon atoms, and Z signifies hydrogen or one or more alkyl, alkoxy or alkylmercapto groups each with 1 to 4 carbon atoms, trifluoromethyl groups or fluorine, chlorine or bromine atoms; of a salt of compound I with a pharmacologically tolerable inorganic or organic acid; and a pharmacologically compatible carrier.

2. A pharmaceutical composition in accordance with claim 1, wherein the dose unit for intravenous administration contains 1 to 50 mg. of said compounds the unit dose for intramuscular administration contains 1 to 50 mg. of said compounds and the unit dose for oral administration contains 1 to 100 mg. of said compounds.

3. A pharmaceutical composition with blood pressure lowering activity suitable for the treatment of hypertension, comprising as active ingredient a pharmaceutically effective amount of an aryl-substituted piperazinyl quinazolone-(4) derivative of the formula I*

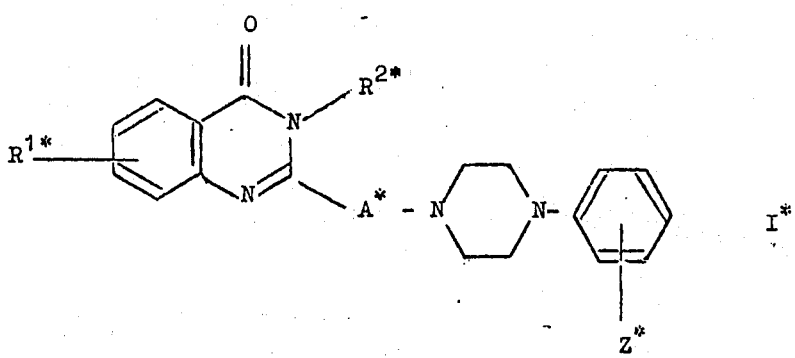

wherein $R^{1*}$ = signifies 1 to 2 methyl, ethyl, methoxy or ethoxy groups, $R^{2*}$ = signifies hydrogen, a methyl or ethyl group, A* signifies an ethylene or trimethylene group, and Z* signifies a fluorine or chlorine atom, a methyl or alkoxy group with 1 to 4 carbon atoms, or a salt of compound I* with a pharmacologically compatible inorganic or organic acid, and a pharmacologically compatible carrier.

4. A pharmaceutical composition with blood pressure lowering activity suitable for the treatment of hypertension, comprising as active ingredient a pharmaceutically effective amount of 2-(2-(1-(2-methoxyphenyl) piperazinyl-4)-ethyl)-6,7-dimethoxy-4(3H)-quinazolone and a pharmacologically compatible carrier.

5. A pharmaceutical composition with blood pressure lowering activity and suitable for the treatment of hypertension, comprising as active ingredient a pharmaceutically effective amount of 2-(2-(1-phenylpiperazinyl-4)ethyl)-6,7-dimethoxy-4(3H)-quinazolinone and a pharmacologically compatible carrier.

6. A pharmaceutical composition with blood pressure lowering activity and suitable for the treatment of hypertension, comprising as active ingredient a pharmaceutically effective amount of 2-(2-(1-phenylpiperazinyl-4)ethyl)-6-chloro-4(3H)-quinazolinone and a pharmacologically compatible carrier.

* * * * *